(12) United States Patent
Knopp et al.

(10) Patent No.: US 8,891,086 B2
(45) Date of Patent: Nov. 18, 2014

(54) OPTICAL SCANNING SYSTEMS AND METHODS FOR MEASURING A SEALED CONTAINER WITH A LAYER FOR REDUCING DIFFUSIVE SCATTERING

(75) Inventors: Kevin J. Knopp, Newburyport, MA (US); Robert L. Green, Haverhill, MA (US); Brendon D. Tower, Weymouth, MA (US); Christopher D. Brown, Haverhill, MA (US); Gregory H. Vander Rhodes, Melrose, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 469 days.

(21) Appl. No.: 12/724,192

(22) Filed: Mar. 15, 2010

(65) Prior Publication Data

US 2010/0315629 A1 Dec. 16, 2010

Related U.S. Application Data

(60) Provisional application No. 61/187,103, filed on Jun. 15, 2009.

(51) Int. Cl.
| | |
|---|---|
| *G01N 21/55* | (2014.01) |
| *G01N 21/65* | (2006.01) |
| *G01J 3/02* | (2006.01) |
| *G01J 3/44* | (2006.01) |
| *G01N 21/47* | (2006.01) |
| *G01N 21/35* | (2014.01) |

(52) U.S. Cl.
CPC ........ *G01N 21/65* (2013.01); *G01N 2021/3595* (2013.01); *G01J 3/0289* (2013.01); *G01J 3/0232* (2013.01); *G01J 3/02* (2013.01); *G01J 3/0291* (2013.01); *G01J 3/0272* (2013.01); *G01J 3/0264* (2013.01); *G01J 3/44* (2013.01); *G01N 21/4738* (2013.01); *G01J 3/0262* (2013.01); *G01N 2201/0221* (2013.01)
USPC ............................ 356/445; 356/440; 356/432

(58) Field of Classification Search
USPC .......................... 356/300–334, 432, 440, 445
See application file for complete search history.

(56) References Cited

U.S. PATENT DOCUMENTS

| | | | |
|---|---|---|---|
| 6,593,582 | B2 | 7/2003 | Lee et al. |
| 6,608,677 | B1 | 8/2003 | Ray et al. |
| 7,057,791 | B2 | 6/2006 | Azimi et al. |
| 7,068,905 | B2 | 6/2006 | Vakhshoori et al. |
| 7,110,109 | B2 | 9/2006 | Knopp et al. |
| 7,116,415 | B2 | 10/2006 | Iuliano |
| 7,180,653 | B2 | 2/2007 | Knopp et al. |
| 7,190,861 | B2 | 3/2007 | Knopp et al. |
| 7,215,836 | B2 | 5/2007 | Vakhshoori et al. |

(Continued)

*Primary Examiner* — Tarifur Chowdhury
*Assistant Examiner* — Michael P Lapage
(74) *Attorney, Agent, or Firm* — Ion C. Abraham (57) ABSTRACT

Disclosed are apparatus, kits, methods, and systems that include a radiation source configured to direct radiation to a sample; a detector configured to measure radiation from the sample; an electronic processor configured to determine information about the sample based on the measured radiation; a housing enclosing the source, the detector, and the electronic processor, the housing having a hand-held form factor; an arm configured to maintain a separation between the sample and the housing, the arm including a first end configured to connect to the housing and a second end configured to contact the sample; and a layer positioned on the second end of the arm, the layer being configured to contact the sample and to transmit at least a portion of the radiation from the sample to the detector.

28 Claims, 4 Drawing Sheets

(56) References Cited

U.S. PATENT DOCUMENTS

| | | |
|---|---|---|
| 7,254,501 B1 | 8/2007 | Brown et al. |
| 7,289,208 B2 | 10/2007 | Vakhshoori et al. |
| 7,351,588 B2 | 4/2008 | Poponin |
| 7,376,346 B2 * | 5/2008 | Merola et al. ............ 396/14 |
| 7,411,670 B2 | 8/2008 | Zribi et al. |
| 7,420,672 B2 | 9/2008 | Wang et al. |
| 7,499,159 B2 | 3/2009 | Knopp et al. |
| 7,548,311 B2 | 6/2009 | Knopp et al. |
| 7,636,157 B2 | 12/2009 | Wang et al. |
| 7,675,611 B2 | 3/2010 | Azimi et al. |
| 7,741,618 B2 | 6/2010 | Lee et al. |
| 7,760,352 B2 | 7/2010 | Armstrong et al. |
| 7,773,645 B2 | 8/2010 | Wang et al. |
| 7,796,251 B2 | 9/2010 | Ponsardin et al. |
| 7,829,345 B1 | 11/2010 | MacDonald |
| 7,833,802 B2 | 11/2010 | Henry et al. |
| 8,597,578 B2 * | 12/2013 | Tan et al. ............ 422/82.11 |
| 2002/0039183 A1 * | 4/2002 | Yagita ............ 356/240.1 |
| 2003/0021124 A1 * | 1/2003 | Elbrecht et al. ............ 362/572 |
| 2004/0106164 A1 * | 6/2004 | Brown et al. ............ 435/14 |
| 2005/0248759 A1 | 11/2005 | Wang et al. |
| 2006/0045151 A1 | 3/2006 | Vakhshoori et al. |
| 2006/0088069 A1 | 4/2006 | Vakhshoori et al. |
| 2006/0170917 A1 | 8/2006 | Vakhshoori et al. |
| 2008/0291426 A1 | 11/2008 | Azimi et al. |
| 2009/0185187 A1 * | 7/2009 | Crist et al. ............ 356/436 |
| 2010/0027007 A1 * | 2/2010 | Adams et al. ............ 356/338 |
| 2010/0302546 A1 | 12/2010 | Azimi et al. |

* cited by examiner

OPTICAL SCANNING SYSTEMS AND METHODS FOR MEASURING A SEALED CONTAINER WITH A LAYER FOR REDUCING DIFFUSIVE SCATTERING

CROSS-REFERENCE TO RELATED APPLICATIONS

This application claims priority to U.S. Provisional Application No. 61/187,103, filed on Jun. 15, 2009, the entire contents of which are incorporated herein by reference.

TECHNICAL FIELD

This disclosure relates to scanning and, in some embodiments, identifying materials.

BACKGROUND

Optical scanning methods such as Raman spectroscopy and infrared spectroscopy can provide useful information about unknown materials. By identifying unknown materials, certain threats posed by hazardous materials can be reduced or eliminated.

SUMMARY

In general, in a first aspect, the disclosure features an apparatus that includes an arm configured to maintain a separation between a sample and a device that measures radiation from the sample, the arm including a first end configured to connect to a housing of the device and a second end configured to contact the sample, and a layer positioned on the second end of the arm, the layer being configured to contact the sample and to transmit at least a portion of the radiation from the sample to the device.

Embodiments of the apparatus can include any one or more of the following features.

The radiation from the sample can include at least one of radiation emitted by the sample, radiation reflected from the sample, radiation transmitted by the sample, and radiation scattered from the sample. The sample can include a container and a material positioned within the container. The radiation from the sample can include radiation from the material positioned within the container.

The layer can include a synthetic material. The layer can include rubber. The layer can include a gel. The layer can include a fluid.

The arm can be formed of at least one of a plastic material, a metal, a rubber material, a glass, and a silicon-based material. The arm can have a truncated conical shape. The arm can include at least one wall and one or more windows positioned in the at least one wall, the windows being configured to permit viewing of an interior portion of the arm. The arm can include a socket formed in a wall of the arm and configured to receive a vial, the socket extending into an interior portion of the arm. The apparatus can include at least one channel formed in the arm, where the at least one channel is configured to transport a portion of the fluid from a reservoir to the second end of the arm.

Embodiments of the apparatus can also include any of the other features disclosed herein, as appropriate.

In another aspect, the disclosure features a system that includes: a radiation source configured to direct radiation to a sample; a detector configured to measure radiation from the sample; an electronic processor configured to determine information about the sample based on the measured radiation; a housing enclosing the source, the detector, and the electronic processor, the housing having a hand-held form factor; an arm configured to maintain a separation between the sample and the housing, the arm including a first end configured to connect to the housing and a second end configured to contact the sample; and a layer positioned on the second end of the arm, the layer being configured to contact the sample and to transmit at least a portion of the radiation from the sample to the detector.

Embodiments of the system can include any one or more of the following features.

The radiation from the sample can include at least one of radiation emitted by the sample, radiation reflected from the sample, radiation transmitted by the sample, and radiation scattered from the sample. The sample can include a container and a material positioned within the container. The radiation from the sample can include radiation from the material positioned within the container.

The layer can include at least one of a rubber material and a gel. The arm can be formed of at least one of a plastic material, a metal, a rubber material, a glass, and a silicon-based material.

The arm can include a socket formed in a wall of the arm and configured to receive a vial, the socket extending into an interior portion of the arm. The system can be configured so that when a vial is inserted into the socket, the detector is configured to measure radiation from a material in the vial, and when a vial is not inserted into the socket, the detector is configured to measure radiation from the sample.

The layer can include a fluid, and the arm can include at least one channel formed therein, the at least one channel being configured to transport a portion of the fluid from a reservoir to the second end of the arm. The reservoir can be formed in the arm.

The arm can include a pin connected to the second end of the arm and extending to contact an electrical switch positioned on or within the housing. The pin can include an extended portion of a wall of the arm. The electrical switch can be coupled to the electronic processor. The system can be configured so that when the arm contacts the sample, the electrical switch is activated. The electronic processor can be configured to cause the radiation source to direct radiation to the sample when the electrical switch is activated. The electronic processor can be configured to cause the detector to measure radiation from the sample when the electrical switch is activated.

The layer can include a deformable material that deforms to at least partially fill voids in a surface of the sample when the arm contacts the sample.

The detector can be configured to measure radiation from the layer, and the electronic processor can be configured to determine spectral information about the layer from the measured radiation from the layer. When a component of the determined information meets a condition relative to a threshold value, the electronic processor can be configured to cause the radiation source to direct radiation to the sample, and to cause the detector to measure radiation from the sample. The component of the determined information can include an amplitude of a peak in the measured radiation. The peak can include a peak in a Raman scattering spectrum of the layer or a peak in an absorption spectrum of the layer.

The arm can be formed from a material that is sufficiently rigid so that, during use, the arm maintains an approximately constant distance between the sample and the housing when the arm contacts the sample.

The electronic processor can be configured to use the spectral information about the layer to calibrate the detector.

Embodiments of the system can also include any of the other features disclosed herein, as appropriate.

In a further aspect, the disclosure features a method that includes: positioning a device that includes a housing, an arm connected to the housing, and a layer positioned on an external surface of the arm so that the layer contacts a sample; directing radiation to the sample from a radiation source positioned within the housing; measuring radiation from the sample with a detector positioned within the housing; and using an electronic processor to determine information about the sample based on the measured radiation.

Embodiments of the method can include any one or more of the following features.

The radiation from the radiation source can pass through the layer prior to reaching the sample. The radiation from the sample can pass through the layer prior to being measured by the detector.

The layer can include at least one of a rubber material or a gel. The layer can include a fluid, and the method can include dispensing a portion of the fluid from a reservoir formed in the arm through one or more channels formed in the arm and onto the exterior surface of the arm prior to positioning the device so that the layer contacts the sample.

The method can include applying a force to the housing to compress a portion of the layer after the layer contacts the sample. Applying the force can activate a switch coupled to the electronic processor, and the method can include causing the radiation source to direct radiation to the sample and causing the detector to measure radiation from the sample when the switch is activated. The method can include monitoring spectral information about the layer, and directing radiation to the sample and measuring radiation from the sample when a component of the spectral information meets a condition relative to a threshold value. The component of the spectral information can include an amplitude of a peak in the spectral information. The peak can include a peak in a Raman scattering spectrum of the layer or a peak in an absorption spectrum of the layer.

The method can include applying a force to the housing so that the layer deforms to at least partially fill voids formed in a surface of the sample. The method can include monitoring spectral information about the layer, and using the spectral information to calibrate the detector prior to measuring at least some of the radiation from the sample.

Embodiments of the method can also include any of the other features or steps disclosed herein, as appropriate.

In another aspect, the disclosure features a kit for detecting a material in a container that includes: a source configured to direct radiation to the container; a detector configured to measure radiation from the material; an arm configured to maintain a spacing between the detector and the container; an optical coupling medium configured to be positioned on a surface of the arm, and further configured to contact the container; and an electronic processor configured to determine information about the sample based on the emitted or reflected radiation.

Embodiments of the kit can include any one or more of the following features.

The optical coupling medium can include an adhesive material. The adhesive material can be flexible and configured to conform to a wall of the container. The adhesive material can be configured to at least partially fill voids in a wall of the container when a force is applied to the adhesive material.

The kit can include a housing enclosing the radiation source and the detector, the housing including a window through which radiation from the source leaves the housing and radiation from the material enters the housing.

The optical coupling medium can include a single adhesive surface, and the single adhesive surface can be configured to contact a wall of the container. The optical coupling medium can include a single adhesive surface, and the single adhesive surface can be configured to contact the aim. The optical coupling medium can include two adhesive surfaces, and a first one of the adhesive surfaces can be configured to contact a wall of the container and the other of the adhesive surfaces can be configured to contact the arm. The optical coupling medium can be configured so that during use, radiation from the source is incident on the optical coupling medium prior to being incident on the container, and the optical coupling medium is configured to transmit more than 50% of the radiation from the source. The optical coupling medium can be configured so that during use, radiation from the material is incident on the optical coupling medium prior to being incident on the detector, and the optical coupling medium is configured to transmit more than 50% of the radiation from the material.

The electronic processor can be coupled to the radiation source and to the detector and configured to direct the radiation source and the detector to measure spectral information about the optical coupling medium. The electronic processor can be configured, when a component of the spectral information meets a condition relative to a threshold, to cause the radiation source to direct radiation to the container, and to cause the detector to measure radiation from the sample. The component of the spectral information can include an amplitude of a peak in the spectral information. The peak can include a peak in a Raman scattering spectrum of the optical coupling medium or a peak in an absorption spectrum of the optical coupling medium. The electronic processor can be configured to use the spectral information about the optical coupling medium to calibrate the detector.

The information about the sample can include at least one of Raman scattering information and absorption information.

Embodiments of the kit can also include any of the other features disclosed herein, as appropriate.

In a further aspect, the disclosure features a method that includes: applying an optical coupling medium to a sample; positioning a device that includes a housing, a window integral to the housing, a radiation source enclosed within the housing, and a detector enclosed within the housing, so that the window contacts the optical coupling medium; directing radiation to the sample from the radiation source; measuring radiation from the sample using the detector; and using an electronic processor to determine information about the sample based on the emitted or reflected radiation.

Embodiments of the method can include any one or more of the following features.

The sample can include a container that includes a material positioned therein.

The optical coupling medium includes an adhesive material. The adhesive material can be flexible and can conform to a surface of the sample. The method can include applying a force to the adhesive material to deform the adhesive material so that the adhesive material at least partially fills voids formed in the surface of the sample.

Applying the optical coupling medium can include positioning the optical coupling medium so that during use, a portion of the radiation from the source and a portion of the radiation from the sample each pass through the optical coupling medium. The method can include measuring spectral information about the optical coupling medium. The method can include, when a component of the spectral information meets a condition relative to a threshold, causing the radiation source to direct radiation to the sample, and causing the detector to measure radiation from the sample. The component of the spectral information can include an amplitude of a peak in the spectral information. The peak can include a peak in a Raman scattering spectrum of the optical coupling medium or a peak in an absorption spectrum of the optical coupling medium. The method can include using the spectral information about the optical coupling medium to calibrate the detector.

Determining information about the sample can include determining at least one of Raman scattering information about the sample and absorption information about the sample.

Embodiments of the method can include any of the other features or steps disclosed herein, as appropriate.

In another aspect, the disclosure features a system that includes: a radiation source configured to direct radiation to a sample; a detector configured to measure radiation from the sample; an electronic processor; and a housing enclosing the radiation source, the detector, and the electronic process, the housing having a hand-held form factor. The electronic processor is configured to determine, within a first time interval, a value of a quantity related to a probability that the sample corresponds to a material in a database of material information. If the value of the quantity is greater than a threshold value, the electronic processor is configured to: cause the radiation source to direct additional radiation to the sample; cause the detector to measure additional radiation from the sample; and determine, based on the additional radiation from the sample, an identity of the sample within a second time interval larger than the first time interval.

Embodiments of the system can include any one or more of the following features.

The first time interval can be 20 seconds or less.

The electronic processor can be configured so that if the value of the quantity is less than the threshold value, the electronic processor halts further analysis of the sample.

Determining the value of the quantity can include identifying a presence or absence of peaks in the measured radiation. The electronic processor can be configured so that if peaks at certain wavelengths are present in the measured radiation, the electronic processor adjusts the quantity to have a value above the threshold value. The electronic processor can be configured so that if peaks at certain wavelengths are not present in the measured radiation, the electronic processor adjusts the quantity to have a value below the threshold value.

The system can include an electronic display coupled to the electronic processor and configured to display a message when the value of the quantity is determined. The message can include an instruction to perform further analysis on the sample if the value of the quantity is greater than the threshold value. The message can include an instruction not to perform further analysis on the sample if the value of the quantity is less than the threshold value. The electronic processor can be configured to display information about the sample on the electronic display, the information about the sample including at least one of the identity of the sample, an identity of one or more components in the sample, a threat status for the sample, handling information for the sample, and instructions to security personnel.

The measured radiation can include Raman scattering information about the sample. Alternatively, or in addition, the measured radiation can include absorption information about the sample.

The detector can include an interferometer, and the electronic processor can be further configured to select a scanning range for the interferometer so that the value of the quantity is determined in the first time interval. If the value of the quantity exceeds the threshold value, the electronic processor can be configured to increase the scanning range of the interferometer.

The electronic processor can be configured to select a measurement time during which the detector measures the radiation from the sample so that the value of the quantity is determined during the first period. If the value of the quantity exceeds the threshold value, the electronic processor can be configured to increase the measurement time.

Determining the value of the quantity can include comparing information derived from the measured radiation to reference information. The reference information can include information about samples to be analyzed further and information about samples not to be analyzed further, and the electronic processor can be configured to compare the information derived from the measured radiation only to reference information corresponding to samples not to be analyzed further. The reference information can include information about samples to be analyzed further and information about samples not to be analyzed further, and the electronic processor can be configured to compare the information derived from the measured radiation only to reference information corresponding to samples to be analyzed further.

The electronic processor can be configured to determine, if the sample includes a plurality of components, values of a plurality of quantities related to probabilities that one or more of the components include a material in a database of material information within the first time interval. The electronic processor can be configured so that if the value of any of the quantities is larger than an associated threshold value, the electronic processor: causes the radiation source to direct additional radiation to the sample; causes the detector to measure additional radiation from the sample; and compares spectral information derived from the additional measured radiation to reference information to determine an identity of at least some of the components in the sample within the second time interval.

The electronic processor can be configured to select the measurement time by: accumulating measurements of radiation from the sample and obtaining an estimate of a variability of the accumulated radiation measurements; accumulating additional measurements of radiation from the sample and obtaining an updated estimate of the variability of the accumulated radiation; continuing the accumulating until the updated estimate of the variability is less than a threshold value; and setting the measurement time based on an elapsed time during which the measurements of radiation were accumulated. Obtaining an estimate of the variability of the accumulated radiation measurements can include determining a signal-to-noise ratio for the accumulated measurements.

Embodiments of the system can also include any of the other features disclosed herein, as appropriate.

In a further aspect, the method includes: directing radiation to a sample; measuring radiation from the sample; determining, within a first time interval, a value of a quantity related to a probability that the sample corresponds to a material in a database of material information based on the measured radiation; and, if the value of the quantity is larger than a threshold value, (i) directing additional radiation to the sample, (ii) measuring additional radiation from the sample, and (iii) determining, based on the additional radiation from the sample, an identity of the sample within a second time interval larger than the first time interval.

Embodiments of the method can include any one or more of the following features.

The method can include setting the value of the quantity to be larger than the threshold value if the measured radiation includes peaks at selected wavelengths. The method can include displaying a message when the value of the quantity is determined. The message includes at least one of a message to perform further analysis on the sample, and a message not to perform further analysis on the sample.

The method can include selecting a measurement time or a scanning range for a detector used to measure the radiation from the sample so that the value of the quantity is determined in 20 seconds or less.

The method can include determining the value of the quantity by comparing information derived from the measured radiation to reference information. The reference information can include information about samples to be analyzed further and samples not to be analyzed further, and the method can include comparing the information derived from the measured radiation to the reference information about samples to be analyzed further.

The method can include displaying information that includes at least one of the identity of the sample, an identity of one or more components in the sample, a threat status for the sample, handling information for the sample, and instructions to security personnel.

Selecting the measurement time can include: accumulating measurements of radiation from the sample and obtaining an estimate of a variability of the accumulated radiation measurements; accumulating additional measurements of radiation from the sample and obtaining an updated estimate of the variability of the accumulated radiation; continuing the accumulating until the updated estimate of the variability is less than a threshold value; and setting the measurement time based on an elapsed time during which the measurements of radiation were accumulated. Obtaining an estimate of the variability of the accumulated radiation measurements can include determining a signal-to-noise ratio for the accumulated measurements.

Embodiments of the method can also include any of the other features or steps disclosed herein, as appropriate.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Scanning systems can be used in a variety of environments to identify unknown materials, to evaluate the threat posed by unknown materials, to provide information and advice regarding clean-up procedures for spilled materials, and to provide general security screening functions. Scanning systems can be implemented in a wide range of sizes, from portable, handheld instruments to larger systems integrated into permanent or semi-permanent structures.

Figure 1:
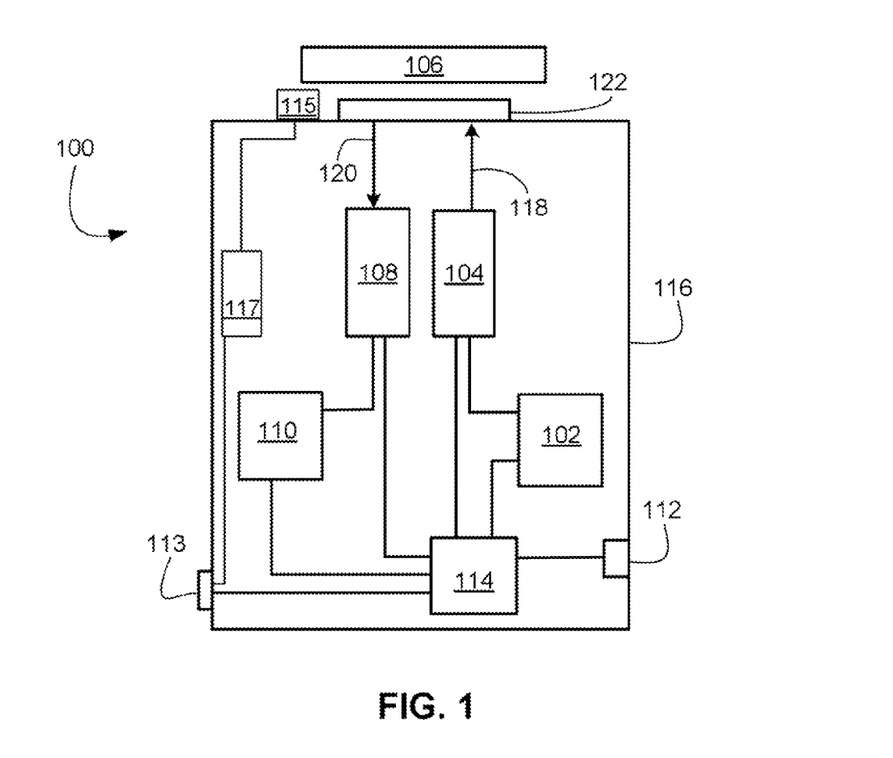
FIG. 1 is a schematic diagram showing an embodiment of a scanning system.

FIG. 1 shows a schematic diagram of a scanning system 100. System 100 includes a radiation source 102 which generates illumination radiation 118. Illumination radiation 118 is directed by illumination optics 104 to be incident on sample 106. Radiation 120 emitted, transmitted, or reflected from sample 106 is directed by receiving optics 108 to enter detector 110, where the radiation is detected and converted to electrical signals. Light source 102, illumination optics 104, receiving optics 108, and detector 110 are each electrically connected to electronic processor 114, which provides control signals and receives information from the various components of system 100 via electronic signal lines. Processor 114 is also connected to a communication interface 112 which can permit wired or wireless communication with one or more external devices and/or systems (e.g., computers, computer networks, network storage devices, external processors). The various elements of system 100 are enclosed within a housing 116.

Figure 2:
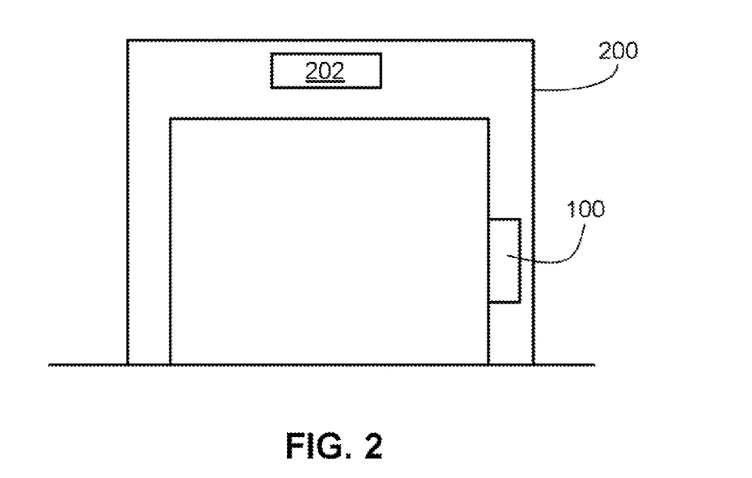
FIG. 2 is a schematic diagram showing another embodiment of a scanning system.

The system shown in FIG. 1 is implemented as a portable, hand-held scanner. In some embodiments, however, scanning systems can be implemented as part of larger permanent or semi-permanent structures. FIG. 2 shows a scanning system 100 implemented as part of a security screening arch 200. Arch 200 can be positioned in an airport or in front of an accessway to a part of a building, for example. A person seeking to enter restricted areas can be compelled to pass under the arch, where scanning system 100 can perform one or more scans of the person. Arch 200 can include a display 202 electrically connected to system 100 (e.g., connected to processor 114), which displays information including scan results, threat information, material identification information, warning information, and other such data to security personnel monitoring access to the restricted area. Arch 200 can also include signaling devices such as flashing lights and/or sound generators that can warn security personnel based on the results of scans performed.

Scanning system 100 can also be implement in other environments. For example, in some embodiments, scanning system 100 is integrated into a product assembly or packaging line in a manufacturing facility. At various stages of manufacture, assembly, or packaging, scanning system 100 can be used to scan the products to verify authenticity, for example. On handheld systems, a system operator typically initiates a scan by pressing a button or engaging (or otherwise activating) a sensor. For example, a switch 117 connected to the sensor can be mounted in a stand-off, nose cone, pin or other member 115 attached to a housing of the system, and the system operator can activate the sensor by touching the switch to a sample and applying pressure (e.g., to the housing) to cause the switch to be depressed. In manufacturing environments, however, scans can be initiated automatically by devices such as photoelectric switches and pressure-sensitive switches.

In general, light source 102 can include any one or more of a variety of different light sources such as light emitting diodes, laser diodes, various types of laser sources, and lamps. Light source 102 can be configured to generate either narrow-bandwidth or wide-bandwidth illumination radiation 118. For example, a full width at half-maximum bandwidth of illumination radiation 118 can be 1 nm or more (e.g., 3 nm or more, 5 nm or more, 10 nm or more, 25 nm or more, 50 nm or more, 75 nm or more, 100 nm or more, 200 nm or more, 300 nm or more, 400 nm or more, 500 or more).

Illumination optics 104 and receiving optics 108 can each include a variety of different optical elements, including lenses, filters, mirrors, dispersive elements such as gratings, polarizers, waveplates, beamsplitters, mechanical and/or opto-electronic shutters, and optical measurement devices such as diodes. Illumination optics 104 and receiving optics 108 can, in some embodiments, share some (or even all) elements in common.

Detector 110 can include any one or more of a variety of different types of detectors. Suitable detectors include photodiodes, CMOS-based detectors, CCD detectors, and photomultiplier tubes. Detector 110 can also include mechanical and/or opto-electronic components such as shutters and slits, and dispersive optical elements such as diffraction gratings, diffractive optics, and holographic gratings. In some embodiments, detector 110 can include thermal detectors such as pyrometers and/or bolometers. Further, in certain embodiments, detector 110 can include one or more optical assemblies for performing other types of detection. As an example, detector 110 can include one or more various types of interferometers (e.g., Michaelson interferometers, Mach-Zehnder interferometers, or other types of interferometers). Interferometric detection can be particularly useful, for example, when measuring spectral infrared absorption and/or reflectance information (e.g., when system 100 functions as a Fourier transform infrared scanning system).

Modes of Operation

Scanning system 100 can operate in one or more modes. In some embodiments, system 100 can be configured to measure Raman scattering responses in a sample. For example, referring to FIG. 1, when sample 106 is positioned close to window 122, light source 102 generates illumination light 118, which passes out of housing 116 through window 122 and is incident on sample 106. A portion of illumination light 118 undergoes Raman scattering in sample 106, and the scattered light enters housing 116 through window 122 as radiation 120, which is detected by detector 110. Detector 110 can process the detected radiation to generate a Raman spectrum of sample 106, which is then transferred to processor 114 for further analysis.

Scanning system 100 can also operate in IR absorption and/or reflectance mode. In this mode of operation, sample 106 is typically positioned in contact with window 122. When illumination light 118 reaches window 122, a portion of the illumination light is absorbed by sample 106, and a portion is reflected from window 122 and collected as radiation 120 by receiving optics 108, and transported to detector 110. Detector 110 can be configured to detect radiation 120 and determine an absorption or reflectance spectrum of sample 106. The absorption spectrum can be transferred to processor 114 for further analysis.

Alternatively, or in addition, a portion of the illumination light that is absorbed by sample 106 can be transmitted through the sample, emerging from the sample on a side opposite the side where the illumination light was incident. Scanning system 100 can be configured to measure the transmitted radiation (e.g., using detector 110) and to determine, based on the measured radiation, an absorption and/or reflectance spectrum of sample 106.

In some embodiments, scanning system 100 can operate in both Raman and IR absorption modes, either alternately or at the same time. Light source 102 can generate illumination radiation 118, which can include a single beam of radiation or multiple beams (e.g., one beam for Raman mode, and one beam for IR absorption mode). Sample 106 is illuminated as disclosed above for each of the modes of operation, and both Raman and absorption spectra for sample 106 are determined by detector 110 (which can include a single detector, or separate detectors dedicated to one of the modes). Processor 114 receives from detector 110 both the Raman and IR absorption spectra of sample 106.

Other modes of operation are also possible. For example, in some embodiments, system 100 can be operated in a fluorescence or phosphorescence mode, where illumination light 118 causes sample 106 to fluoresce and/or phosphoresce, and detector 110 measures the fluorescence and/or phosphorescence spectrum of sample 106.

In general, a wide variety of different samples can be interrogated by system 100. Exemplary samples include materials housed in shipping containers, materials uncontained on a floor, articles of clothing, bags and other carrying devices, materials packaged as pills, and foods. When the spectral information (e.g., Raman information, absorption information) has been received by processor 114, the processor initiates a comparison of the information against established reference information (e.g., a spectral library) to assess the nature of sample 106.

Compensation for Ambient Light

The scanning systems disclosed herein can be used in a variety of environments where the intensity of ambient light is significant. System 100 can be configured to compensate for the effects of ambient light on the measured spectral data. For example, in systems configured for the Raman mode of operation, light source 102 can be cycled on and off multiple times between subsequent scans (e.g., by opening and closing a shutter in illumination optics 104 and/or receiving optics 108). Detector 110 can measure signals with the shutter both closed and open, so that a background signal amplitude (e.g., as a function of wavelength) representing the ambient light can be determined, and subsequently used to compensate measured Raman spectral information.

Alternatively, or in addition, in some embodiments, system 100 can include separate detection elements configured to measure ambient light. For example, system 100 can include, in addition to detector 110, a second detector that is not positioned to measure light that is emitted, transmitted, or reflected by the sample. Instead, the second detector is positioned to detect ambient light in the environment around system 100. The second detector can transmit measurements of ambient light to electronic processor 114, which can combine the ambient light information with measurement information from detector 110 to yield corrected measurement information. Referring again to FIG. 1, for example, system 100 includes an ambient light sensor 113 connected to processor 114. Processor 114 can initiate measurements of ambient light (e.g., to determine the intensity of ambient light, the spectral properties of ambient light) via sensor 113.

Similarly, for systems configured for IR absorption and/or reflectance mode, spectral data can be measured both with sample 106 in contact with window 122, and with sample 106 spaced from sample 122, and the difference between the spectral information obtained in each case can be used to correct IR absorption spectra for the effects of ambient light.

In some embodiments, wavelength-dependent information about ambient light and/or incident light, determined as disclosed above, can be combined with wavelength-dependent calibration information about system 100 to estimate the wavelength-dependent variability of Raman and/or IR absorption spectra measured using system 100. For example, in addition to receiving spectral information about sample 106 from detector 110, processor 114 can also receive spectral ambient light information. Combining the ambient light information with stored calibration information, processor 114 can determine wavelength-dependent variability information for spectra measured with system 100. Both the measured spectral information and the variability information can be used to assess sample 106.

Material Assessment and Identification

Processor 114 assesses and identifies samples by comparing the measured spectral information to established reference information (e.g., a library of spectral information) that includes information for a variety of different materials. A variety of different techniques are available for performing the comparison, including both direct mathematical "nearest neighbor" type comparisons, and probability-based assessments. Probability-based assessments can make use of the variability information disclosed above.

Comparisons against a large library of different materials can be time-consuming in some circumstances. However, in certain implementations such as in airports, at building entrances and entrances to other secure areas, and in manufacturing environments, material assessment and/or identification must be performed within a limited time window (e.g., a window of about 10-20 s or less). When scanning system 100 is implemented in such an environment, the system can be operated in one of several modes to provide an assessment within the prescribed time window.

In certain embodiments, for example, scanning system 100 can be configured for two-stage assessment of samples. The first stage of the assessment can be a rapid assessment stage that focuses on a limited subset of available spectral and/or library information to make an initial determination regarding the sample. Depending upon the results of the initial determination, a second, more detailed assessment stage can then be initiated to provide a more thorough determination regarding the sample.

For example, in some high-throughput screening embodiments, the first analysis stage can be based on the presence or absence of a relatively small number of peaks or other features (e.g., one, two, three, four peaks) in the measured spectral information for the sample. The presence or absence of these features can be used to immediately report the sample as a threat or a material that requires further investigation. The material can be separated (e.g., by diverting to another path on a manufacturing line, or by isolating a person from a security line) and subjected to either the second, more detailed analysis stage, or to manual inspection (e.g., by a line worker or security personnel).

To realize a relatively rapid first stage of assessment, scanning system 100 can be configured in different ways depending upon the nature of the data to be acquired. For example, in some embodiments, the first analysis stage is based on Raman spectral information acquired for the sample. Scanning system 100 can acquire Raman spectral information during a time-limited window, e.g., by measuring signals with detector 110 for a limited period of time. Due to the limited time window, spectral features (e.g., peaks) may not be as well resolved as they would be during longer scans. However, system 100 can use the acquired spectral information to complete the first stage of analysis of the sample.

In some embodiments, scanning system 100 can perform the first analysis stage based on infrared spectral information (e.g., infrared absorption and/or reflectance by the sample). The infrared spectral information can be acquired, for example, by a detector 110 that includes an interferometer. During high resolution data acquisition, the interferometer can be scanned over a relatively wide range (e.g., a range of relative delays) to acquire spectral information. However, during the first analysis stage, the interferometer can be scanned over a smaller range (e.g., corresponding to an abbreviated temporal window) to complete the first stage of data acquisition more rapidly. Spectral information (e.g., in the form of an interferogram) can be transformed (e.g., by Fourier transformation) to yield transformed spectral information, which can then be used to assess the sample in the first analysis stage. Typically, by scanning the interferometer over a smaller range, the transformed spectral information has lower resolution than spectral information acquired by scanning over the full range of the interferometer. However, the first analysis stage can still be completed on the basis of the lower resolution information, resulting in a relatively rapid initial assessment of the sample.

To ensure that the first stage of the analysis is rapid, scanning system 100 can be configured to operate in a binary first assessment stage. For example, in security screening, it is frequently the case that only a limited number of materials are prohibited from entering a secure area. Therefore, the system's reference information (e.g., spectral library) can be restricted to include only those prohibited materials, and the first stage assessment can be configured to determine only whether a sample in question appears to include one or more prohibited materials. Alternatively, or in addition, the reference information can include only allowable materials, and the first stage assessment can determine only whether a sample in question appears to include only allowable materials, or whether the sample includes at least one material not present in the reference information (and therefore, not allowable). The result of the first stage of analysis is binary: either a decision to "allow" (e.g., the sample does not appear to contain a material on the restricted list, or the sample appears to contain only materials that are allowable) or to "deny" (e.g., the sample appears to include at least one material on the restricted list, the sample appears to include at least one material that does not appear among the allowable materials, or the results of the first stage assessment are indeterminate and a second state of analysis is needed).

Where a sample is a mixture of more than one type of material, the first stage of assessment can be terminated as soon as at least one component of the mixture corresponds to an entry on the list of prohibited materials. That is, to save time, it is not necessary to which ones of a potentially large set of materials are prohibited and which are not. As soon as one material is identified as prohibited, processor 114 can issue a warning to "deny" the entire sample.

In some embodiments, the decision to "allow" or "deny" can be made, in whole or in part, on the basis of certain spectral features such as peaks in the measured spectral information, rather than on the basis of complete spectral measurements. For example, spectral peaks appearing at certain wavelengths can indicate the presence of certain chemical functional groups or moieties in the materials that compose a particular sample. It may not be necessary to conclusively identify the materials to determine that they should be prevented from entering a secure area. Thus, upon identifying the presence or absence of certain peaks in the first stage of assessment, system 100 can be configured to issue either an "allow" signal or a "deny" signal.

Figure 6:
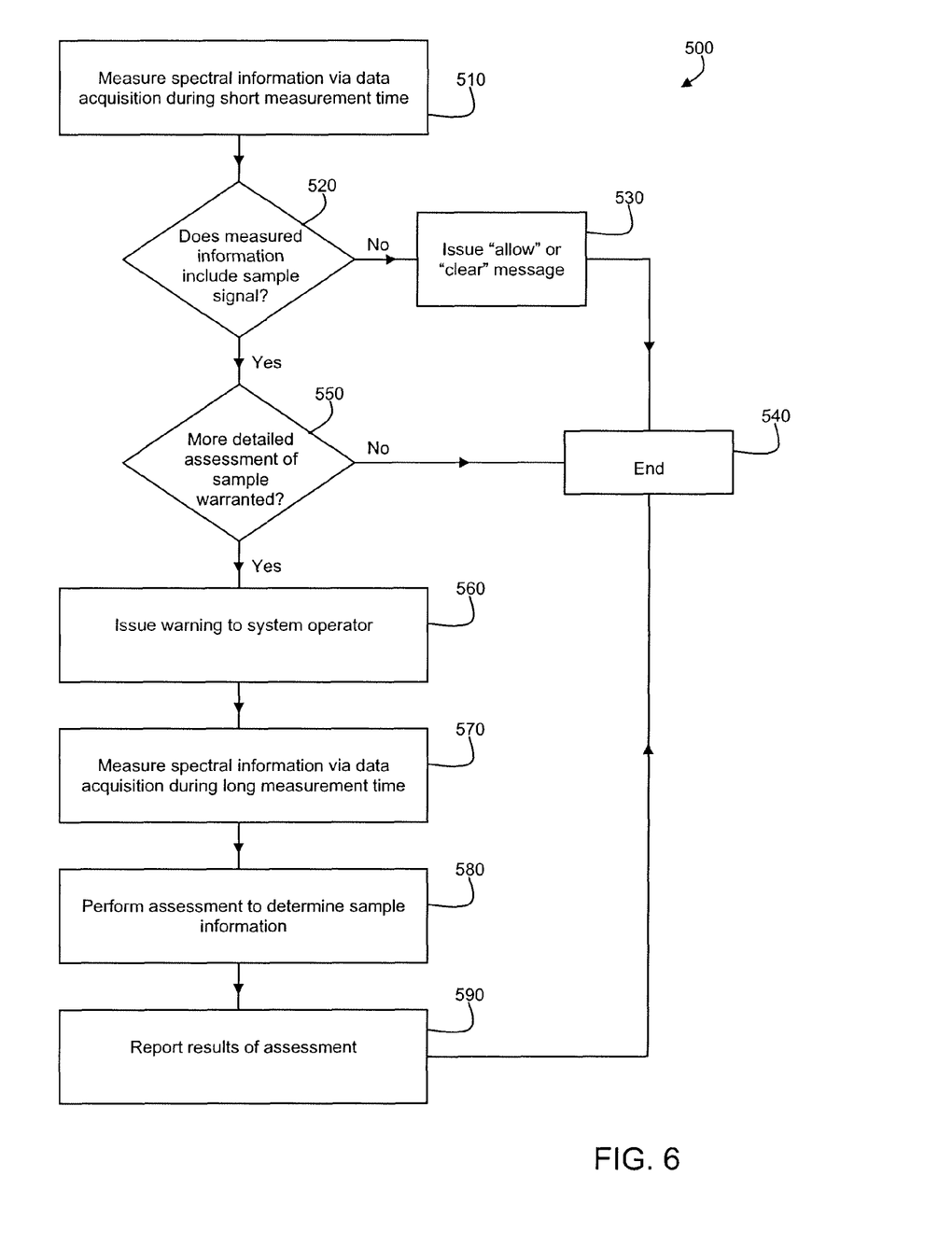
FIG. 6 is a flow chart showing steps in two-stage sample analysis and assessment.

FIG. 6 is a flow chart 500 that shows a series of steps for two-stage sample analysis and assessment. In initial step 510 of the flow chart, sample spectral information is measured relatively rapidly during a short time interval by a system configured to assess the sample (e.g., system 100). Following acquisition of the initial spectral information in step 510, the spectral information is analyzed in step 520 to determine whether the information includes measurable signals attributable to the sample. For example, in some embodiments, system 100 operates in Raman measurement mode, and the spectral information is analyzed in step 520 to determine whether sufficient Raman scattering information is present to assess the sample. Alternatively, or in addition, in certain embodiments, system 100 operates in infrared measurement mode, and the spectral information is analyzed in step 520 to determine whether sufficient infrared absorption and/or reflectance information is present to assess the sample. If sufficient information is not present, the system can issue a "clear" or "allow" signal to a system operator in step 530, and then terminate the analysis in step 540. In certain embodiments, the system may conclude in step 530 that the sample consists primarily of water, and can issue a message to the system operator stating this conclusion.

However, if sufficient information is present in step 520 to continue the assessment, system 100 is configured to perform a first stage assessment of the sample in step 550 to determine whether a more detailed analysis is warranted. The first stage assessment in step 550 can include, for example, comparing the spectral information to reference information to determine identity information about the sample (e.g., an identity of one or more components in the sample; a determination that the sample includes multiple different components; a determination that the sample might be a threat and merits further examination; a determination that the sample contains or may contain compounds having certain reactive, toxic, hazardous, or other dangerous properties; a determination that the sample contains or may contain certain types of chemical moieties that may pose a threat). As a result of the first stage assessment in step 550, system 100 may determine that the sample does not merit further examination, and the analysis procedure can terminate at step 540. Alternatively, system 100 may determine that the sample does warrant further investigation in a second stage of analysis. Steps 510-550 discussed above typically comprise the first stage of the two-stage analysis shown in FIG. 6; typically, as discussed above, this first stage of analysis occurs relatively rapidly, e.g., step 550 can be complete in a time period of one minute or less (e.g., 50 seconds or less, 40 seconds or less, 30 seconds or less, 20 seconds or less, 10 seconds or less).

Completing step 550 within a relatively short time period can be important in certain implementations, particularly where a large number of subjects are to be scanned. For example, in certain security screening applications and/or in manufacturing applications (e.g., product scanning and screening), only a limited amount of time is available to obtain an initial assessment of each subject. By performing step 550 within a relatively short time period as discussed above, a suitable first-stage assessment can be obtained, while at the same time, a relatively high scanning throughput rate can be maintained.

Steps 560-590 constitute the second stage of the two-stage analysis procedure. In optional step 560, having determined that further investigation of the sample is warranted, system 100 can issue a message to the system operator advising that the sample may be a threat, based on the first analysis stage. In step 570, system 100 measures additional spectral information for the sample, typically over a longer data acquisition time to obtain higher quality data (e.g., data having less noise and/or greater resolution and/or more identifiable spectral features). In step 580, system 100 performs a second stage assessment of the higher quality data acquired in step 570 to determine sample information such as a threat status for the sample, an identity of the sample, a composition of the sample, handling information for the sample, security measures that should be enacted, and other such information. In step 590, system 100 reports some or all of the determined sample information to the system operator (e.g., via a display screen and/or alerts such as warning noises, flashing lights, messages transmitted to monitoring stations). The second stage of the analysis then terminates at step 540.

System 100 can also be configured to operate in authentication mode to enable high-throughput scanning. In authentication mode, system 100 is configured to determine only whether sample 106 corresponds to one or more of a significantly limited set of materials. When spectral information is received from detector 110, processor 114 compares the spectral information against library information corresponding to the limited set of candidate materials, and reports whether or not a match is achieved with any one or more of the candidates. By restricting the set of candidates significantly (e.g., system 100 can be configured to authenticate unknown samples against a list of one, two, three, four, five, six, eight, ten materials), authentication can be achieved rapidly.

In some embodiments, acquisition times can be adjusted to ensure that spectral information is of sufficient quality before a comparison to reference information (e.g., a spectral library) is performed. The comparison to reference information is generally a time-consuming aspect of material assessment and identification; accordingly, performing the comparison before the spectral information is of sufficient quality for comparison wastes analysis time. Instead, by adjusting acquisition time to ensure that spectral information is of sufficient quality before the comparison is made, thereby reducing or eliminating wasted time performing comparisons to reference information when the spectral information is of insufficient quality, the overall assessment can be completed in a shorter period of time To ensure that the spectral information is of sufficient quality, repeated scans of the sample can be performed and combined. After each successive scan, or after a series of successive scans, a measure of the wavelength-dependent variability of the spectral information can be obtained. This measure can be obtained, for example, by calculating an estimated variability as a function of wavelength for the spectral information. Alternatively, the spectral variability can be measured directly from the data, e.g., by making a measurement of a signal-to-noise ratio (S/N) as a function of wavelength. Scanning of the sample and cumulative combination of the spectral information can continue until a threshold S/N ratio, or another variability threshold, is reached. Once reached, the cumulative spectral information can be compared to library information. The threshold can be determined automatically by processor 14, for example, or selected manually by a system operator.

Where system 100 is configured for operation within a specific time window, cumulative successive scans can be continued until a certain threshold spectral variability is reached, as discussed above, or until a selected time window has elapsed. The time window can be selected automatically by processor 114, or manually by a system operator. In certain embodiments, if the time window limit is reached and the spectral variability (e.g., S/N) remains below threshold, the sample can be "cleared" by system 100, indicating that no sufficiently-strong Raman, absorption, or other response was measurable. Processor 114 can report this result to a system operator via a display screen and one or more warning messages and/or signals.

In some embodiments, system 100 does not identify the sample (e.g., based on the sample's composition), but instead only identifies the sample as a threat, or not a threat. In certain embodiments, system 100 can also be configured to identify a sample as a possible threat (e.g., meriting further examination). That is, system 100 does not necessarily identify the sample as corresponding to a particular material or component/mixture of components, but instead, based on certain features of the sample identified from the measured spectral information, system 100 classifies the sample as a threat, not a threat, or a potential threat. System 100 can be configured to report these determinations to a system operator (as discussed further below). The system can also be configured to report information such as a suspected class(es) of the sample based on the measured spectral information (e.g., one or more chemical classes such as oxidizers, fluorinated compounds, energetic materials). In some embodiments, the assessment of a sample as a threat may be based, as discussed further below, at least in part on features of the measured spectral information without direct comparison to reference information. For example, system 100 can identify certain spectral features in the measured spectral information as common to a certain class of compounds that constitute a threat, and can classify that sample as a threat based on the spectral features.

Reporting Information

Figure 3:
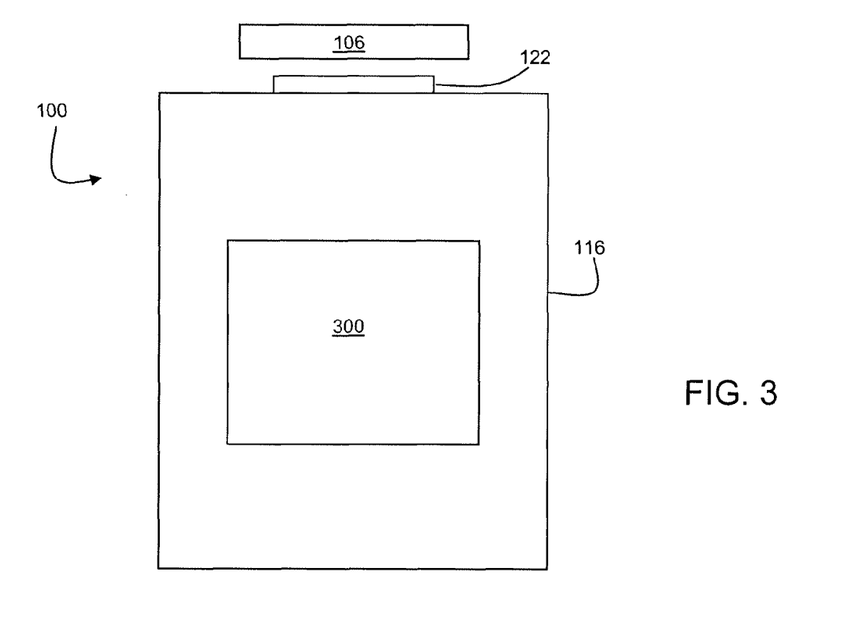
FIG. 3 is a schematic diagram showing an external view of the system of FIG. 1.

System 100 can be configured to report a wide variety of information to a system operator via one or more display screens. FIG. 2 shows an embodiment in which system 100 is linked to an overhead display screen 202. FIG. 3 shows an exterior view of the embodiment of system 100 shown in FIG. 1. A display screen 300 is embedded within housing 116 of system 100, and is electrically connected to processor 114 (connections not shown).

Processor 114 can be configured to display information in a number of different ways via display 300. In some embodiments, processor 114 can display color-coded reporting screens depending on the results of sample assessment. For example, when system 100 determines that sample 106 is composed of only one type of material, and system 100 identifies the material, the results of the analysis can be reported on a green screen. When the system determines that sample 106 includes multiple materials, each of which is identified, then the analysis results can be displayed on a blue screen. A yellow screen can be used to report that a conclusive identification could not be achieved, and can provide information about the library entries that appear to most closely match the sample. A red screen can be used to report that the nature of the sample is uncertain, and no library entries were sufficiently close to merit reporting as possible matches. A confidence level threshold can be used to control whether possible identifications are close enough to report on a yellow screen, or insufficiently close so that the nature of the sample remains uncertain. The confidence threshold can be hard-coded in processor 114, or can be set by a system operator.

In certain embodiments, processor 114 can display either an "allow" signal (e.g., a check mark on a green screen) or a "deny" signal (e.g., an "X" on a red screen) for each sample. This mode of reporting is particularly useful in security screening applications and in high-throughput manufacturing applications.

In some embodiments, processor 114 can be configured to display hazard information in addition to, or as an alternative to, identification information. For example, when system 100 determines that a sample includes one or more dangerous materials, processor 114 can display hazard information such as exposure warnings, clean-up instructions, quarantine requirements, medical/emergency treatment information, chemical reactivity information, and general handling instructions. In certain embodiments, identification information may not be displayed at all; the only information displayed may be safety and/or clean-up instructions. Hazard information can be stored in a database storage unit in system 100 which is linked to processor 114. The stored information can be updated periodically by connecting to one or more external databases via communication interface 112. Alternatively, or in addition, when processor 114 identifies a dangerous material, processor 114 can initiate a link to one or more external databases to retrieve information about the material. Processor 114 can also notify external security monitoring stations to alert personnel stationed there that a dangerous material has been identified. In certain embodiments, processor 114 can issue warnings to security personnel to close and/or lock doors, gates, and other accessways. In some embodiments, processor 114 can initiate and/or complete such procedures automatically.

In some embodiments, processor 114 can be programmed to determine hazard information for materials even if such information is not available in the system's on-board database or in an externally accessible database. Based on the spectral information for the sample—and in particular, based on an identification of spectral features such as peaks corresponding to particular chemical functional groups or moieties in the sample, processor 114 can estimate properties such as flammability, reactivity, and chemical incompatibilities for the sample. Machine-learning algorithms such as a neural networks, and/or statistical learning techniques, can be trained to use the identified spectral features to predict sample properties.

Scanning Through Container Walls

Many samples include materials that are contained within sealed containers. Due to the hazards posed by unknown materials, it is desirable to be able to scan and assess such a material without opening its container. However, many such containers are formed of materials that are translucent; some even have roughened surfaces that diffuse incident light. The quality of spectral information that can be obtained for a particular material is directly related to the ability to direct illumination radiation through the container walls and onto the material therein, and to the ability to capture radiation emerging from the container and direct the radiation to detector 110. Diffusive container walls make both irradiation of the interior material and capture of reflected or scattered radiation more difficult, adversely affecting the quality of spectral information obtained for the material.

Scattering by container walls can be reduced or eliminated by using an optical coupling medium between system 100 and the container walls. The optical coupling medium can be implemented in various ways, but in each implementation, diffusive scattering by the container walls is reduced, enabling improved radiation transmission.

In some embodiments, the optical coupling medium can be implemented as a fluid, a semi-solid, or a gel positioned on an exterior surface of the container. Various fluids can be used, including water. Similarly, various gels are suitable for use, particularly those that do not appreciably alter the spectral properties of either illumination radiation 118 or radiation 120.

In certain embodiments, an adhesive sticker can be applied to the exterior surface of a container to provide the optical coupling medium. Adhesive materials such as tape are particularly useful if, as above, they do not appreciably alter the spectral properties of either illumination radiation 118 or radiation 120.

Figure 4:
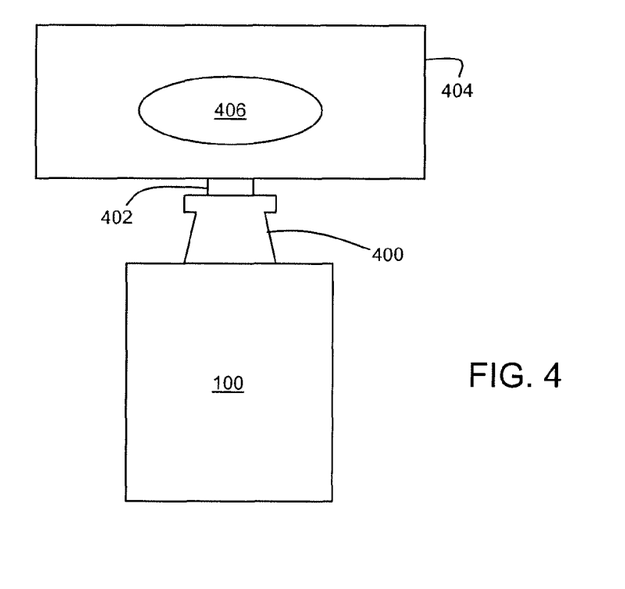
FIG. 4 is a schematic diagram showing a nose cone attachment that includes an optical coupling layer.

In some embodiments, system 100 can include a nose cone attachment that features a rubber or gel pad positioned at the cone apex to provide a window for the passage of illumination radiation 118 and radiation 120. During operation, the nose cone is pressed into contact with the wall of a container. The deformable rubber or gel pad partially fills voids and crevices in the container surface, effecting an improved optical coupling between the container and system 100 in which diffusive scattering by the container is reduced. FIG. 4 shows an embodiment of a nose cone attachment 400 that fits onto system 100. Attachment 400 includes a rubber or gel pad 402 at its apex. Pad 402 is pressed into contact with a wall of container 404, enabling interrogation of material 406 positioned therein. Typically, nose cone attachment 400 is detachable from system 100 so that system 100 can be used either with or without the nose cone. However, in some embodiments, the nose cone is an integral component of system 100 and is formed, for example, from a material component that also forms at least a portion of a housing that encloses system 100.

In certain embodiments, as discussed above, nose cone 400 can include a switch connected to processor 114. When nose cone 400 is pressed into contact with a wall of container 404, for example, the switch is activated. Processor 114, in response to this activation, can initiate one or more actions (including any of the actions discussed herein) such as directing system 100 to measure information associated with sample 406 in container 404.

Nose cone attachment 400 can typically be formed from a variety of materials, including one or more plastic materials, metal materials, rubber materials, deformable inorganic materials such as silicones, and/or glass materials. In FIG. 4, nose cone attachment 400 has a truncated conical shape. More generally, however, attachment 400 can have a variety of different shapes, including cylindrical, rectangular prismatic, angular prismatic, and other regular and/or irregular shapes. Attachment 400 can include one or more windows formed in an exterior wall of the attachment to permit visual inspection of the interior of attachment 400. In certain embodiments, attachment 400 can include a mounting area configured to admit a vial that can hold a sample for analysis. When a vial is inserted into attachment 400, system 100 can measure spectral information for a sample in the vial. Alternatively, with no vial in attachment 400, system 100 can be configured to obtain spectral information by pressing attachment 400 into contact with a wall of a container as discussed above, for example. Other features and aspects of attachment 400 are disclosed, for example, in U.S. Pat. No. 7,636,157, the entire contents of which are incorporated herein by reference.

Figure 5:
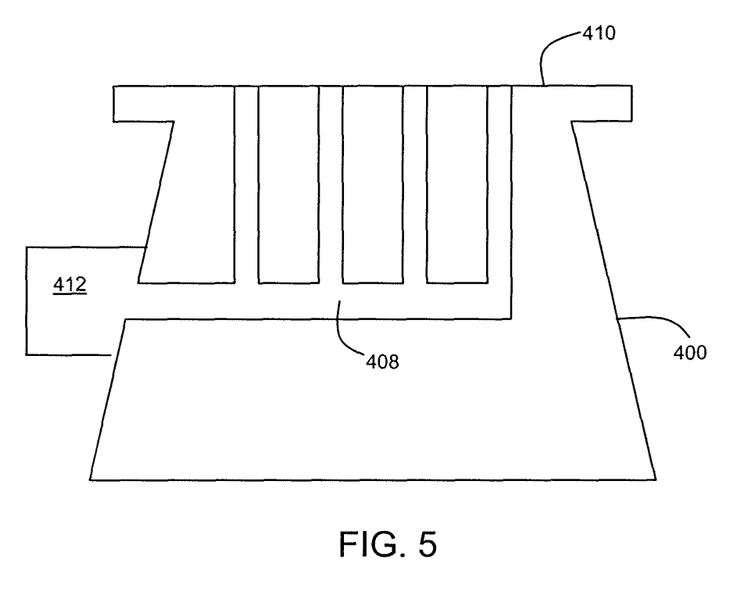
FIG. 5 is a schematic diagram showing another embodiment of a nose cone attachment.

In certain embodiments, rather than a rubber or gel pad 402, nose cone 400 can include a microfluidic delivery system that includes a fluid reservoir 412 and a plurality of fluid transport channels 408. During use, optical coupling fluid is transported from reservoir 412 to contact surface 410 of cone 400 via channels 408. Contact surface 410 is then pressed against the wall of a container, and the fluid delivered to surface 410 forms an optical coupling between cone 400 and the container wall. By using a refillable reservoir, a variety of different coupling fluids can be used, and the amount of fluid discharged can be controlled to account for container walls of different roughness. In general, the microfluidic system can also include valves, channel connectors, and other fluid transport elements. Fluid transport through the microfluidic delivery system can be regulated manually by a system operator, or can be controlled automatically by processor 114, which can be electrically connected to, and communicate with, some or all of the elements of the microfluidic delivery system, including a pump source or other device configured to initiate movement of fluid from reservoir 412 through channels 408.

The various implementations of the optical coupling medium ensure that system 100 can be used without modification of its internal optical components. Specifically, illumination optics 104 and receiving optics 108 do not have to be spatially isolated from one another to eliminate reflected radiation from container walls, for example. Further, the optical coupling medium can be used with other scanning systems different from system 100; like system 100, other scanning systems require little to no modification to implement the optical coupling medium, saving both time and expense while improving the ability of such systems to scan materials through container walls. As a result, any scanning system that interrogates samples through the walls of a container or through a translucent scattering member might be adapted to use the coupling media disclosed herein.

A variety of different materials can be used as the optical coupling medium. Generally, as discussed above, it is advantageous if the optical coupling medium does not appreciably alter the spectral properties of either illumination radiation 118 or radiation 120. Further, optical coupling media that do not have an appreciable Raman or IR absorption/reflectance response in the wavelength region of interest are also preferred. However, in some embodiments, optical coupling media that do have an appreciable Raman or IR absorption/reflectance response in the wavelength region of interest can also be used.

In some embodiments, if the optical coupling medium has a measurable Raman or IR absorption response, the measured response can be used to trigger a scan of the material inside the container. As the optical coupling medium is compressed against the wall of the container, it spreads laterally and thins out. As a result, the measured Raman or IR absorption spectrum of the medium will decrease in intensity. This decrease can be monitored by detector 110 and processor 114; when the spectral response is low enough, a scan of the material inside the container can be initiated. Further, the spectrum of the optical coupling medium, if observable, can be used as internal standard to calibrate detector 110. By first measuring the spectral response of the coupling medium and comparing to the known spectrum of the medium, the detector's calibration can be verified before spectral information about the material within the container is obtained. It can be advantageous if the spectral response of the coupling medium is located in a different portion of the electromagnetic spectrum from the sample spectral response, as discrimination between the two responses is facilitated under this arrangement. However, the spectral response of the coupling medium can be used as an internal standard even when it appears in a common portion of the electromagnetic spectrum with the sample spectral response.

The following U.S. patents and patent applications are incorporated herein by reference in their entirety: U.S. Pat. No. 7,254,501; U.S. patent application Ser. No. 11/837,284, filed on Aug. 10, 2007; and U.S. Pat. No. 7,675,611.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A system for scanning and assessing a sample, the sample comprising a sealed container and a sample material disposed within the sealed container, the sealed container having an interior and an exterior, the system comprising:
   a radiation source configured to direct radiation from the exterior of the sealed container to the sample material disposed within the interior of the sealed container, the sealed container having a wall with an exterior surface;
   a detector configured to measure, through the wall of the sealed container, radiation from the sample material disposed within the interior of the sealed container;

an electronic processor configured to determine information about at least the sample material based on the measured radiation;

a housing external to the sealed container and enclosing the radiation source, the detector, and the electronic processor, the housing having a hand-held form factor;

an arm configured to maintain a separation between the exterior surface of the wall of the sealed container and the housing, the arm including a first end connected to the housing and a second end; and a layer positioned on the second end of the arm, the layer being configured to contact the exterior surface of the wall of the sealed container, a deformable material that deforms to at least partially fill voids in the exterior surface of the wall of the sealed container when the layer contacts the exterior surface of the wall of the sealed container, the layer being operative to transmit at least a portion of the radiation from the sample material disposed within the interior of the sealed container through the wall of the sealed container to the detector, and to reduce diffusive scattering caused by the wall of the sealed container.

2. The system of claim 1, wherein the radiation from the sample material comprises at least one of radiation emitted by the sample material, radiation reflected from the sample material, radiation transmitted by the sample material, and radiation scattered from the sample material.

3. The system of claim 1, wherein the layer comprises at least one of a rubber material and a gel.

4. The system of claim 1, wherein the arm is formed of at least one of a plastic material, a metal, a rubber material, a glass, and a silicon-based material.

5. The system of claim 1, wherein the arm comprises a pin connected to the second end of the arm and extending to contact an electrical switch positioned on or within the housing.

6. The system of claim 5, wherein the pin comprises an extended portion of a wall of the arm.

7. The system of claim 5, wherein the electrical switch is coupled to the electronic processor so that when the arm contacts the the exterior surface of the wall of the sealed container, the electrical switch is activated.

8. The system of claim 5, wherein the electronic processor is configured to cause the radiation source to at least one of direct radiation to the sample, and cause the detector to measure radiation from the sample, when the electrical switch is activated.

9. The system of claim 1, wherein the detector is configured to measure radiation from the layer, and the electronic processor is configured to determine spectral information about the layer from the measured radiation from the layer.

10. The system of claim 9, wherein the electronic processor is configured to use the spectral information about the layer to calibrate the detector.

11. The system of claim 1, wherein, when a component of the determined information meets a condition relative to a threshold value, the electronic processor is configured to cause the radiation source to direct radiation to the sample, and to cause the detector to measure radiation from the sample.

12. The system of claim 11, wherein the component of the determined information comprises an amplitude of a peak in the measured radiation, and wherein the peak comprises a peak in a Raman scattering spectrum of the layer or a peak in an absorption spectrum of the layer.

13. The system of claim 1, wherein the arm is formed from a material that is sufficiently rigid so that, during use, the arm maintains an approximately constant distance between the exterior surface of the wall of the sealed container and the housing when the layer contacts the exterior surface of the wall of the sealed container.

14. The system of claim 1, wherein the arm has a conical shape.

15. A method of scanning and assessing a sample, the sample comprising a sealed container and a sample material disposed within the sealed container, the sealed container having an interior and an exterior, the method comprising:

positioning a device comprising, within a housing, a radiation source, a detector, and an electronic processor, an arm being connected to the housing, and a layer being positioned on an external surface of the arm so that the layer contacts an exterior surface of a wall of the sealed container, the layer comprising a deformable material that deforms to at least partially fill voids in the exterior surface of the wall of the sealed container when the layer contacts the exterior surface of the wall of the sealed container, the arm maintaining a separation between the exterior surface of the wall of the container and the housing, the sample material being disposed within the interior of the container;

directing, by the radiation source, radiation from the exterior of the container to the sample material disposed within the interior of the container;

measuring, through the wall of the container by the detector, radiation from the sample material;

transmitting, through the wall of the container by the layer, at least a portion of the radiation from the sample material disposed within the interior of the container to the detector;

reducing, by the layer contacting the exterior surface of the wall of the container, diffusive scattering caused by the wall of the container; and using an electronic processor to determine information about at least the sample material based on the measured radiation.

16. The method of claim 15, wherein the layer comprises a fluid, the method further comprising dispensing a portion of the fluid from a reservoir formed in the arm through one or more channels formed in the arm and onto the external surface of the arm prior to positioning the device so that the layer contacts the exterior surface of the wall of the container.

17. The method of claim 15, further comprising applying a force to the housing to compress a portion of the layer after the layer contacts the exterior surface of the wall of the sealed container.

18. The method of claim 17, wherein applying the force activates a switch coupled to the electronic processor, the method further comprising causing the radiation source to direct radiation to the sample material and causing the detector to measure radiation from the sample material when the switch is activated.

19. The method of claim 15, further comprising monitoring spectral information about the layer, and using the spectral information to calibrate the detector prior to measuring at least some of the radiation from the sample material.

20. A kit for detecting a sample, the sample comprising a sealed container and a sample material disposed within the container, the container having an interior and an exterior, the kit comprising:

a radiation source configured to direct radiation from the exterior of the sealed container to the sample material disposed within the interior of the container, the sealed container having a wall with an exterior surface;

a detector configured to measure, through the wall of the sealed container, radiation from the sample material disposed within the interior of the container;

an arm configured to maintain a spacing between the detector and the exterior surface of the wall of the container;

an optical coupling medium configured to be positioned on a surface of the arm, and to contact the exterior surface of the wall of the sealed container, the optical coupling medium comprising a deformable material that deforms to at least partially fill voids in the exterior surface of the wall of the sealed container when the optical coupling medium contacts the exterior surface of the wall of the sealed container, the optical coupling medium being operative to transmit at least a portion of the radiation from the sample material disposed within the interior of the sealed container through the wall of the sealed container to the detector, and to reduce diffusive scattering caused by the wall of the container; and an electronic processor configured to determine information about at least the sample material based on the measured radiation emitted by the sample material or reflected from the sample material.

21. The kit of claim 20, wherein the optical coupling medium comprises an adhesive material.

22. The kit of claim 21, wherein the adhesive material is flexible and configured to conform to the exterior surface of the wall of the container.

23. The kit of claim 20, wherein the optical coupling medium comprises a single adhesive surface, and wherein the single adhesive surface is configured to contact one of the exterior surface of the wall of the container, and the arm.

24. The kit of claim 20, wherein the optical coupling medium comprises two adhesive surfaces, and wherein a first one of the adhesive surfaces is configured to contact the exterior surface of the wall of the container and the other of the adhesive surfaces is configured to contact the arm.

25. The kit of claim 20, wherein the optical coupling medium is configured so that during use, radiation from the source is incident on the optical coupling medium prior to being incident on the container, and the optical coupling medium is configured to transmit more than 50% of the radiation from the source.

26. The kit of claim 20, wherein the arm has a conical shape.

27. A method of scanning and assessing a sample, the sample comprising a sealed container and a sample material disposed within the sealed container, the sealed container having an interior and an exterior, the method comprising:

applying an optical coupling medium to an exterior surface of a wall of the sealed container, the optical coupling medium comprising a deformable material that deforms to at least partially fill voids in the exterior surface of the wall of the sealed container when the optical coupling medium is applied to the exterior surface of the wall of the sealed container;

positioning a device comprising, within a housing, a radiation source, a detector, and an electronic processor, an arm being connected to the housing, a window formed in an external surface of the arm, and a layer being positioned on the external surface of the arm so that the window formed in the external surface of the arm contacts the optical coupling medium applied to the exterior surface of the wall of the sealed container, the arm maintaining a separation between the exterior surface of the wall of the sealed container and the housing;

directing, by the radiation source, radiation from the exterior of the sealed container to the sample material disposed within the interior of the sealed container;

measuring, through the wall of the container by the detector, radiation from the sample material, the sample material being disposed within the interior of the sealed container;

transmitting, through the wall of the sealed container by the layer, at least a portion of the radiation from the sample material disposed within the interior of the sealed container to the detector;

reducing, by the layer positioned on the external surface of the arm, diffusive scattering caused by the wall of the sealed container; and using an electronic processor to determine information about at least the sample material based on the measured radiation emitted by the sample material or reflected from the sample material.

28. The method of claim 27, wherein the applying of the optical coupling medium to the exterior surface of the wall of the container comprises positioning the optical coupling medium so that during use, a portion of the radiation from the radiation source and a portion of the radiation from the sample material each pass through the optical coupling medium.

* * * * *